(12) United States Patent
Klopfenstein et al.

(10) Patent No.: US 9,095,020 B2
(45) Date of Patent: Jul. 28, 2015

(54) GENERATOR SUITABLE FOR POWERING A DENTAL CURING LIGHT

(75) Inventors: Denis Klopfenstein, Morges (CH); Daniel Baour, Rolle (CH); James Fowler, Rolle (CH)

(73) Assignee: OZONE TECHNOLOGIES LTD, St. Julian (MT)

( * ) Notice: Subject to any disclaimer, the term of this patent is extended or adjusted under 35 U.S.C. 154(b) by 316 days.

(21) Appl. No.: 13/824,233

(22) PCT Filed: Sep. 13, 2011

(86) PCT No.: PCT/EP2011/065869
§ 371 (c)(1),
(2), (4) Date: May 17, 2013

(87) PCT Pub. No.: WO2012/035024
PCT Pub. Date: Mar. 22, 2012

(65) Prior Publication Data
US 2013/0221863 A1    Aug. 29, 2013

(30) Foreign Application Priority Data
Sep. 16, 2010    (EP) .................................. 10177186

(51) Int. Cl.
| | |
|---|---|
| H05B 37/00 | (2006.01) |
| H05B 39/00 | (2006.01) |
| H05B 41/14 | (2006.01) |
| H05B 33/08 | (2006.01) |
| B06B 1/02 | (2006.01) |
| A61C 1/07 | (2006.01) |
| A61C 13/15 | (2006.01) |

(52) U.S. Cl.
CPC .......... H05B 33/0809 (2013.01); B06B 1/0253 (2013.01); H05B 33/0818 (2013.01); A61C 1/07 (2013.01); A61C 19/003 (2013.01); Y02B 20/346 (2013.01)

(58) Field of Classification Search
USPC .............................................. 315/200 R, 224
See application file for complete search history.

(56) References Cited

U.S. PATENT DOCUMENTS

| | | | | |
|---|---|---|---|---|
| 3,586,936 | A * | 6/1971 | McLeroy ...................... | 318/118 |
| 3,668,486 | A * | 6/1972 | Silver ............................ | 318/116 |
| 4,141,608 | A * | 2/1979 | Breining et al. ......... | 310/316.01 |
| 4,156,157 | A * | 5/1979 | Mabille .................... | 310/316.01 |

(Continued)

FOREIGN PATENT DOCUMENTS

| | | |
|---|---|---|
| EP | 2 230 027 A1 | 9/2010 |
| FR | 2 391 001 A1 | 12/1978 |

*Primary Examiner* — Adam Houston
(74) *Attorney, Agent, or Firm* — Sughrue Mion, PLLC

(57) ABSTRACT

The generator for a piezoelectric motor is also suitable for powering a high power LED for a dental polymerisation lamp via a rectifier, and comprises two transformers each including a primary winding and a secondary winding and four switches controlled by an ultrasonic reference oscillator, two switches being arranged to alternately connect the secondary windings of the two transformers to the piezoelectric load, and the other two switches being arranged to alternately connect the two primary windings to a voltage supply so that during the positive alternation, the primary winding of one of the transformers is charged with energy whereas the secondary winding of the other transformer is discharged into the piezoelectric load, and so that during the negative alternation, the secondary winding of the first transformer discharges the energy thereof whereas the primary winding of the first transformer is charged.

8 Claims, 3 Drawing Sheets

(56) References Cited

U.S. PATENT DOCUMENTS

| | | | | |
|---|---|---|---|---|
| 4,184,092 A | * | 1/1980 | Wieser | 310/316.01 |
| 4,221,994 A | * | 9/1980 | Friedman et al. | 315/224 |
| 4,256,987 A | * | 3/1981 | Takeuchi et al. | 310/316.01 |
| 4,371,816 A | * | 2/1983 | Wieser | 318/118 |
| 2005/0077453 A1 | * | 4/2005 | Kato | 250/221 |
| 2007/0190479 A1 | * | 8/2007 | Jackson et al. | 433/29 |
| 2008/0233541 A1 | * | 9/2008 | De Vreese et al. | 433/216 |
| 2010/0231090 A1 | * | 9/2010 | Klopfenstein et al. | 310/317 |
| 2010/0254149 A1 | * | 10/2010 | Gill | 362/373 |
| 2013/0221863 A1 | * | 8/2013 | Klopfenstein et al. | 315/200 R |
| 2014/0038124 A1 | * | 2/2014 | Gill et al. | 433/29 |
| 2015/0004556 A1 | * | 1/2015 | Jin et al. | 433/29 |

\* cited by examiner

GENERATOR SUITABLE FOR POWERING A DENTAL CURING LIGHT

CROSS REFERENCE TO RELATED APPLICATIONS

This is a National Phase Application in the United States of International Patent Application PCT/EP2011/065869 filed Sep. 13, 2011, which claims priority on European Patent Application No. 10177186.3 of Oct. 16, 2010. The entire disclosures of the above patent applications are hereby incorporated by reference.

FIELD OF THE INVENTION

The present invention concerns a generator for powering a piezoelectric transducer and which is also suitable for powering a high power LED for a dental polymerisation lamp via a rectifier. It further concerns a device comprising the aforementioned generator and a dental polymerisation lamp including a rectifier.

PRIOR ART

In dentistry, photosensitive composites are commonly used, particularly to fill dental caries and other holes in teeth. To achieve this, a dental composite liquid or paste is first of all placed on or in a tooth, and the composite is then irradiated by a lamp so that it polymerises and hardens. To this end, there are known dental polymerisation lamps, which include LEDs (light emitting diodes) for producing the luminous energy necessary for polymerisation. Some LED manufacturers also propose high power LEDs emitting a coloured light called "dental blue light" whose spectrum is limited to a relatively narrow band around the wavelength of 460 nm. One advantage of these "dental blue light" LEDs is that they produce relatively little parasitic heat and are thus suitable for insertion straight into the patient's mouth.

To operate, the LEDs of a dental polymerisation lamp must be connected to an electrical power supply typically supplying a continuous voltage of around 10 to 20 volts and around fifteen watts of power. However, it will be clear that these values are only given by way of example and that the supply voltage depends, amongst other things, on the number of LEDs contained in the lamp, and on the way in which the LEDs are interconnected.

In dentistry, ultrasonic dental equipment can also be used. This equipment is used by dentists for descaling or more generally for removing any deposits on the surface of teeth. Usually, ultrasonic dental equipment takes the form of a handpiece in which an ultrasonic insert, forming the actual vibrating tool, is mounted. A piezoelectric transducer is also arranged in the handpiece to produce an ultrasonic vibration and to communicate the vibration to the insert.

In order to work, the piezoelectric transducer of the ultrasonic equipment must be connected to an electric power supply supplying an alternating voltage at ultrasonic frequency and up to several hundred volts. In a known manner, the handpiece may be connected to the electric power supply by a flexible lead. Moreover, a connector may be arranged at the junction between the handpiece and the lead, to enable the handpiece to be detached, in particular to be cleaned or sterilised.

The Mectron S.R.L. company has recently started selling a versatile electric ultrasonic generator which can be connected to two types of handpieces operating in a completely different manner: both handpieces used as ultrasonic equipment and handpieces used as dental polymerisation lamps. One advantage of having this type of versatile electric generator is that it is no longer necessary to have two separate electric power supplies, one for the ultrasonic tool and the other for the polymerisation lamp.

The use of a single versatile generator instead of two gives rise to some difficulties. Indeed, in order to work, the ultrasonic equipment requires an alternating voltage of several tens of kHz and several hundred volts. Conversely, the dental polymerisation lamp only normally requires a continuous voltage of around ten volts to operate. To overcome this difficulty and to power the polymerisation lamp with a generator provided for an ultrasonic apparatus, one possible solution is to arrange a circuit in the lamp for lowering the voltage and converting the alternating voltage into continuous voltage.

This solution also gives rise to certain difficulties. In fact, most generators for a piezoelectric transducer behave as described in FR Patent No. 2,391,001. FIG. 1 annexed hereto, taken from this prior art document, is a diagram showing the delivered power P according to the transducer impedance Z, respectively in the case of minimum power (curve I), intermediate power (curve II), and maximum power (curve III). Referring to the intermediate power curve II, it is seen that while the transducer impedance Z remains less than threshold Zb, the power P delivered to the transducer increases proportionally to the impedance. If the impedance exceeds the reference threshold, the constant current generator is blocked and the voltage generator is unblocked. From this point on, the delivered power decreases according to a hyperbolic law as the impedance increases. It is clear thus that the usual power generators for piezoelectric transducers have the drawback of only supplying maximum power for a very precise transducer impedance value (as evidenced by the generally triangular shape of curves I and II of FIG. 1A). It is therefore clear that, to power a polymerisation lamp, it is not sufficient simply to lower and rectify the voltage. It is also necessary to check that the impedance of the load, formed by the lamp and the circuit for lowering the voltage, is adapted to the generator.

It is therefore an object of the present invention to supply an electric ultrasonic generator able to power a dental polymerisation lamp wherein the delivered power does not depend substantially on the load impedance, and another object of the present invention is to supply an electric ultrasonic generator able to power a dental polymerisation lamp, which does not require the insertion of a circuit to lower the voltage between the generator and the lamp.

SUMMARY OF THE INVENTION

The present invention achieves this object by providing a generator conforming to the annexed claim 1.

BRIEF DESCRIPTION OF THE DRAWINGS

Other features and advantages of the invention will appear upon reading the following description, given solely by way of non-limiting example, with reference to the annexed drawings, in which.

DETAILED DESCRIPTION OF ONE EMBODIMENT

Figure 2:
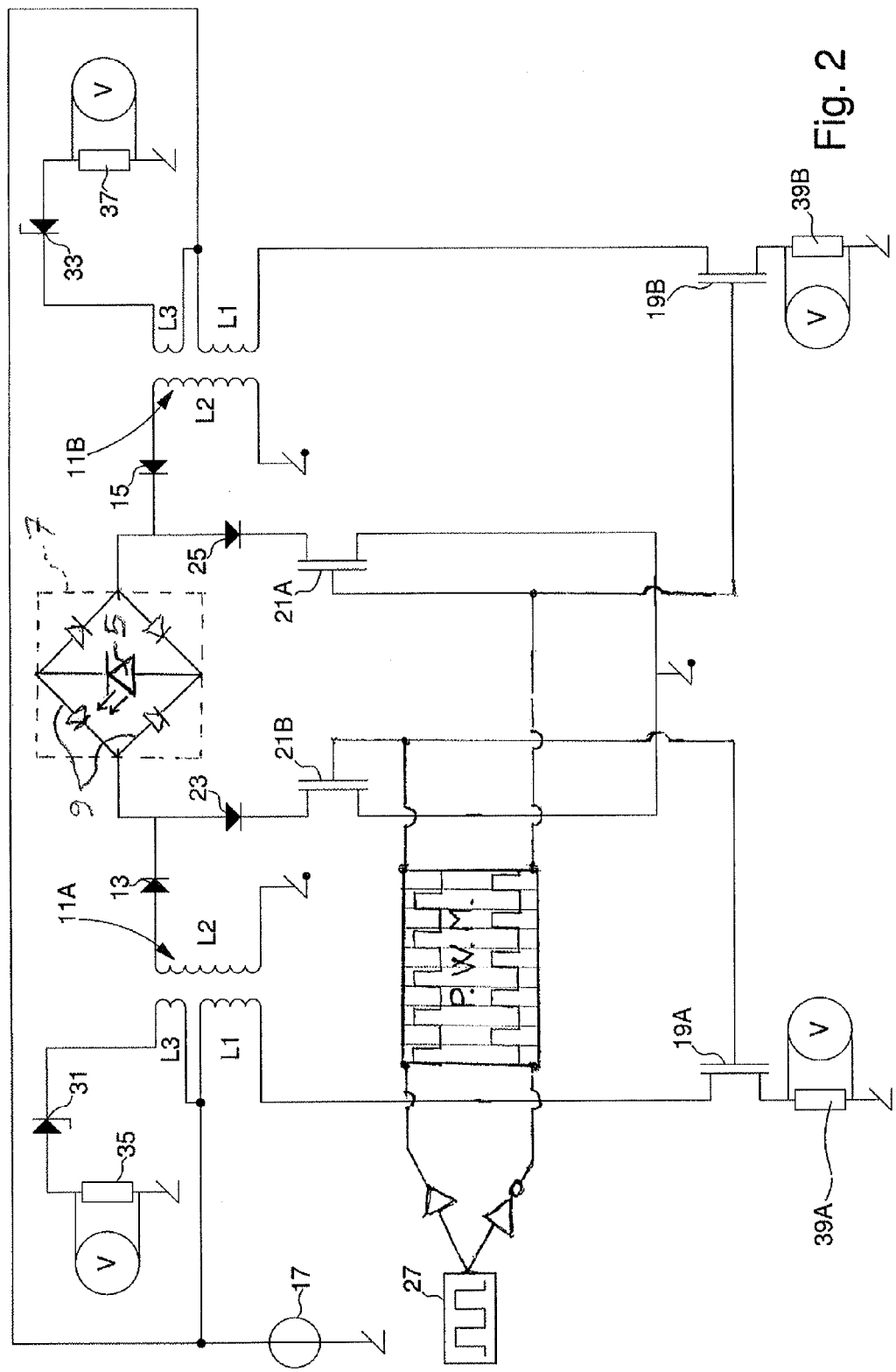
FIG. 2 is an electric diagram of an embodiment of the invention.

FIG. 2 is an electric diagram of a particular embodiment of the generator of the invention, the output of which is connected to a high power LED 5 of a dental polymerisation lamp 7. Lamp 7 is also provided with a rectifier 9. The generator for powering a dental polymerisation lamp 7 includes two transformers 11A and 11B each comprising a primary winding L1 and a secondary winding L2. Each of the two secondary windings L2 is connected by one of the terminals thereof to one of the two terminals of lamp 7, with a diode (13 or 15) also being inserted between each secondary winding and the lamp. The other terminal of each of the secondary windings L2 is connected to earth.

Each of the primary windings L1 of transformers 11A and 11B is series connected with a switch (19A or 19B), between the terminals of a power supply. In the present example, the power supply is formed by a voltage source referenced 17, one terminal of which is connected to each of primary windings L1 and the other terminal is connected to earth. Switches 19A and 19B, like the other switches mentioned in this description, are electrically controlled switches which may be implemented in the form of transistors. These switches will be referred to simply as "switches" below. In addition to being connected to the secondary windings L2 of the two transformers, the two terminals of lamp 7 are also connected to earth via a diode 23 and a switch 21B, respectively a diode 25 and a switch 21A. In other words, lamp 7 is series connected with diode 13, diode 25 and switch 21A between the terminals of secondary winding L2 of transformer 11A, and lamp 7 is also series connected with diode 15, diode 23 and switch 21B, between the terminals of secondary winding L2 of transformer 11B.

Switches 19A, 21B are arranged to be controlled by a first periodic control signal, termed here a "direct" signal, whereas switches 19B and 21A are arranged to be controlled by a second periodic control signal which is phase shifted by a semi-period relative to the first periodic signal, and which is termed here the "inverse" signal. In the present example, a means (not shown) controls the duration of the periodic pulses forming the first and second control signals. This pulse width modulation (PWM) preferably acts on both signals, so that the periodic pulses of the two control signals both have the same duration.

From the following description, those skilled in the art will understand that the power supplied by the generator depends on the pulse duration, and that the PWM means thus controls the power supplied by the generator. It should be specified, however, that the present invention is not limited to a generator whose power is controlled by PWM. Indeed, according to another embodiment, the power supplied by the generator could for example be set once and for all. Alternatively, it is also possible to control the power supplied by the generator by adjusting the voltage supplied by power supply 17, or by varying the frequency of the first and second periodic control signals. As regards this latter possibility, it is important to note that, unlike a piezoelectric transducer, a dental polymerisation lamp does not form a resonant circuit, but only a resistive circuit (in other words, the characteristics of the polymerisation lamp connected to a generator do not determine the frequency at which the generator has to operate).

Figure 3A:
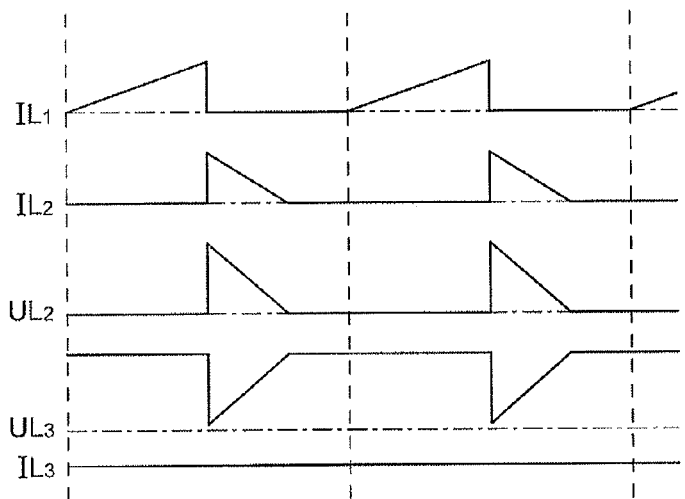
FIGS. 3A, 3B and 3C are graphs showing the current and voltage in the windings of the transformers of the generator of FIG. 2 for three load impedance values.

Switches 19A and 21B are closed throughout the duration of the "direct" signal pulses. Throughout the duration of the "inverse" signal pulses, it is switches 19B and 21A which are closed. During an "inverse" signal pulse, the circuit formed by the secondary winding L2 of transformer 11A, lamp 7, diodes 13 and 25 and switch 21A is closed and the energy stored in transformer 11A is transferred to the load. Simultaneously, switch 19B is closed and primary winding L1 of transformer 11B is directly connected to voltage source 17. The current through the primary winding produces an increase in magnetic flux. Energy is therefore stored in the magnetic circuit. During a "direct" signal pulse the reverse is true. Secondary winding L2 of transformer 11B gives back its energy by discharging into the circuit including lamp 7, diodes 15 and 23 and switch 21B, whereas the current through primary winding L1 of transformer 11A causes energy to be stored in its magnetic circuit. The graph of FIG. 3A shows the behaviour of the current and the voltage in windings L1, L2 and L3 of one of the two transformers 11A or 11B in an example case where the duration of a pulse is exactly equal to a semi-period. It is seen that current IL1 in the primary winding of the transformer regularly increases for an alternation before dropping back to zero and remaining there for the duration of the next alternation. The secondary winding takes over at the transition between two alternations. It is seen that a current IL2, of decreasing intensity, flows through secondary winding. In the example illustrated, the current IL2 flows until the stored energy has completely dissipated. The variations of intensity in current IL2 are accompanied by corresponding variations in voltage UL2 between the terminals of the secondary winding.

It is clear that the fact of having two transformers 11A and 11B and connecting lamp 7 alternately to one and then the other transformer results in an alternating supply voltage being supplied to the lamp. Moreover, those skilled in the art will appreciate that, in short, the function of switches 19A, 19B, 21A, 21B is to control transformers 11A and 11B so that they operate in flyback mode.

Figure 3B:
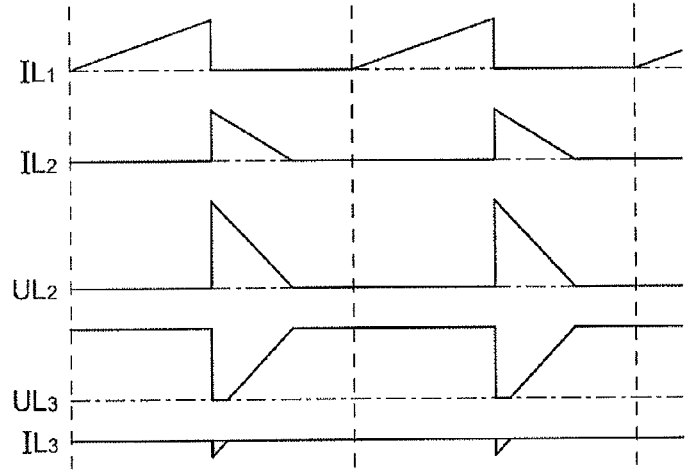
Figure 3C:
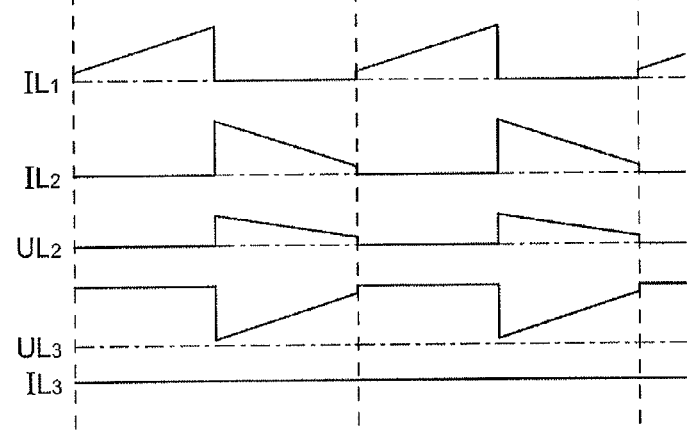

It may happen that the load impedance is insufficient to dissipate all of the energy stored in the transformer. This situation is illustrated by the graph in FIG. 3C. Referring to this graph, it can be seen that, when the load impedance is particularly low, current IL2 and voltage UL2 do not have time to drop back to zero before the end of an alternation. It can also be seen that the energy not dissipated in the secondary winding is in the primary winding at the start of the next alternation. This non-dissipated energy is responsible for the non-zero intensity of current IL1 in primary winding L1 at the start of the alternation (FIG. 3C). It will thus be clear that, below a certain threshold, the smaller the impedance, the greater the intensity of current IL1 will be in the primary winding.

FIG. 2 also shows two measuring circuits 39A and 39B. These measuring circuits are each arranged to measure the current in the primary winding (L1) and one of the two transformers 11A and 11B. Basically, the current measured by the measuring circuits is a function of the impedance of the load connected to the generator. This measurement may thus be used to regulate the generator. In particular, any trapezoidal current shape (IL1, FIG. 3C) is a sign that part of the energy has not been dissipated and remains in the transformer from the preceding alternation. Moreover, the current measurement can detect, for example, any short-circuits or a resonant frequency, or can also automatically determine the type of load connected to the generator (resonant circuit or resistive circuit).

FIG. 2 also shows that transformer 11A and 11B each include a tertiary winding L3. Winding L3 of transformer 11A is series connected with a diode 31 and a resistor 35, between voltage source 17 and earth. Likewise, winding L3 of transformer 11B is series connected with diode 33 and a resistor 37, between voltage source 17 and earth. As will be seen in more detail below, the function of windings L3 is to limit the maximum voltage supplied at the output of secondary winding L2.

The speed with which the current intensity in L2 decreases when the energy stored in one of the transformers is transferred to the load naturally depends on the impedance associated with the load. The higher the impedance, the more quickly the current intensity decreases, and the higher the voltage between the terminals of the secondary winding will be. The FIG. 3B graph shows the behaviour of the generator of FIG. 2 in a situation where the impedance of the load connected to the generator is particularly high. FIG. 3B shows that the intensity of current IL2 decreases substantially more quickly than in FIG. 3A. Moreover, voltage UL2 at the start of an alternation is also considerably higher than in the case of FIG. 3A. It will be clear that if, for one reason or another, the impedance of lamp 7 becomes very large (because of a burnt out component in the circuit, for example), the output voltage UL2 is liable to increase to the point of damaging the generator. This is the reason why, in the present example, the two transformers 11A and 11B each include a third winding L3 which is inductively coupled to the primary and secondary windings L1 and L2.

Referring again to FIG. 2, it is seen that diodes 31 and 33 are connected to windings L3 by their cathode and connected to earth by their anode. Since the other terminal of each winding L3 is connected to the positive terminal of voltage source 17, the diodes are normally subject to a negative voltage UL3. In these conditions, diodes 31 and 33 prevent the current from passing through. However, if the voltage induced in L3 exceeds the continuous supply voltage, the voltage UL3 remaining across the diodes becomes temporarily positive, and a current IL3 can start to flow in L3. This transitory current IL3 has the effect of limiting voltage UL2 at the terminals of winding L2. The presence of winding L3 thus allows to limit voltage UL2 at a value which is determined by selecting the ratio between the induction values L2 and L3.

Figure 1A:
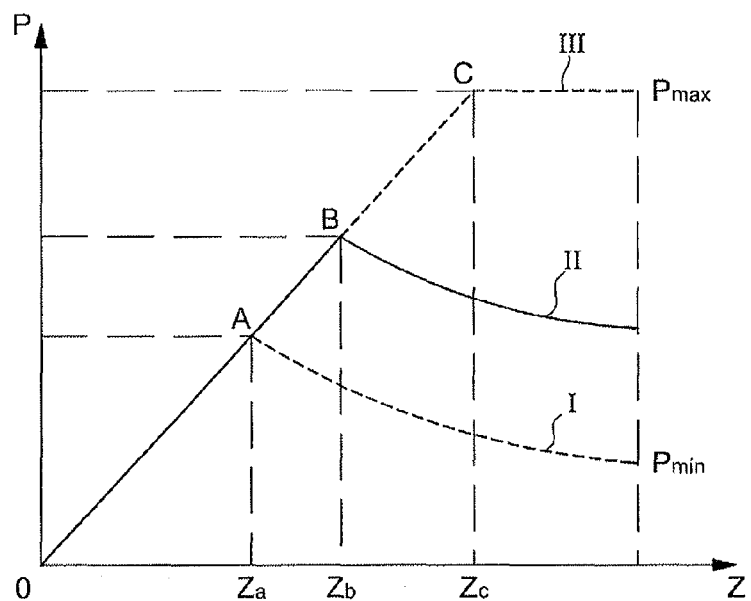
FIG. 1A is a graph showing the power delivered by a state of the art generator for a piezoelectric transducer according to the impedance of the piezoelectric transducer.
Figure 1B:
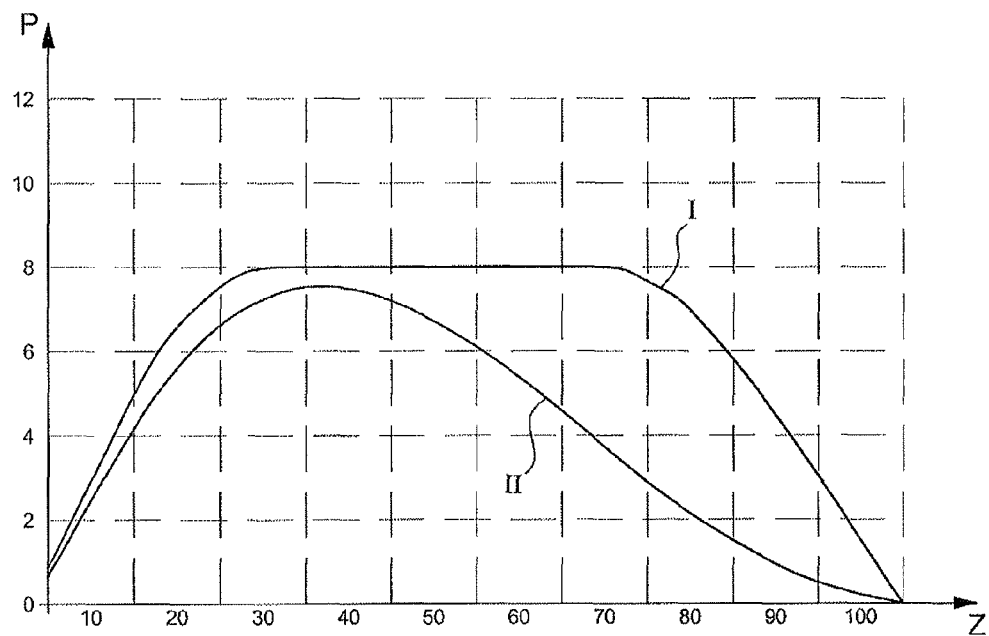
FIG. 1B is a graph comparing the power delivered by a generator of the present invention according to the load impedance with that delivered in the same circumstances by a prior art generator.

FIG. 1B is a graph including a first curve, which shows the behaviour of the power supplied by the generator which has just been described according to the piezoelectric transducer impedance. The graph also includes a second curve, which shows the behaviour of the power of a prior art generator for a piezoelectric transducer such as that described in the aforementioned FR Patent No. 2,391,001. FIG. 1B shows that the first curve includes a first increasing portion, a second constant portion and finally a third decreasing portion. The second portion occupies all of the central part of the graph and thus corresponds to medium impedance values. In this range, the power supplied by the generator according to the invention is substantially constant, and the behaviour of the generator corresponds to that shown by the graph in FIG. 3A. The first portion of the curve is for impedance values which are insufficient to dissipate all of the energy stored in the transformers prior to the end of an alternation. This first portion of the curve is for a range in which the behaviour of the generator corresponds to that shown in the graph in FIG. 3C. Within this range, the power supplied is reduced in proportion to the impedance. The third portion of the curve is for the highest impedances. The generator behaviour in this area corresponds to that described by the graph in FIG. 3B. In this area, the voltage between the terminals of secondary winding L2 is limited by winding L3 and the current thus decreases progressively as the impedance increases.

The first curve of FIG. 1B thus demonstrates that the power supplied at the output by a generator according to the invention is substantially constant for a large load impedance value range. When the generator powers a piezoelectric transducer, this feature of the invention enables the transducer to be supplied with constant power independently of any fluctuations in the mechanical load to which the piezoelectric transducer is subject. Moreover, when an LED of a dental polymerisation lamp (whose impedance is much smaller) is substituted for the piezoelectric transducer, the power supplied by the generator is not affected.

The invention claimed is:

1. A generator for powering a piezoelectric transducer and also suitable for powering a high power LED for a dental polymerisation lamp via a rectifier, comprising two transformers each including a primary winding and a secondary winding and four switches controlled by an ultrasonic reference oscillator, two switches being arranged to alternately connect the secondary windings of the two transformers to the piezoelectric load, and the other two switches being arranged to alternately connect the two primary windings to a voltage supply so that during a first alternation, called the "positive" alternation, the primary winding of one of the transformers is charged with energy whereas the secondary winding of the other transformer is discharged into the piezoelectric load, and so that during a second alternation, called the "negative" alternation, the secondary winding of the first transformer discharges the energy thereof whereas the primary winding of the first transformer is charged.

2. The generator according to claim 1, wherein it includes a means of controlling the power supplied by the generator.

3. The generator according to claim 2, wherein the means of controlling the power uses pulse width modulation.

4. The generator according to claim 2, wherein the means of controlling the power modulates the voltage supplied by said voltage supply and/or the frequency of the first and second periodic control signals.

5. The generator according to claim 1, wherein each transformer includes a third winding maintained at a fixed voltage and a diode in series with the third winding so as to limit the negative voltage between the terminals of the third winding.

6. The generator according to claim 1, wherein at least one of the transformers includes a circuit for measuring the current in the primary winding arranged to detect any trapezoidal shape of the current which would be a manifestation of the presence of non-dissipated energy remaining from the preceding alternation.

7. The generator according to claim 5, wherein at least one of the transformers includes a circuit for measuring the current in the third winding, arranged to detect whether the third winding is allowing a current to pass, and thus to detect whether the negative voltage between the terminals of the third winding has been limited.

8. The electronic device for a dentist comprising a generator according to claim 1, said generator being connected to at least one high power LED via a rectifier.

* * * * *